United States Patent [19]

Mikkelson

[11] Patent Number: 4,576,161

[45] Date of Patent: Mar. 18, 1986

[54] INSTRUMENT FOR USE IN OBSTRUCTING THE VAS DEFERENS

[76] Inventor: Vernon E. Mikkelson, 27001 Calaroga Ave., Hayward, Calif. 94545

[21] Appl. No.: 592,136

[22] Filed: Mar. 22, 1984

[51] Int. Cl.[4] ............................................. A61B 17/00
[52] U.S. Cl. ................................ 128/303 R; 128/321; 128/346
[58] Field of Search ................... 128/303 R, 305, 321, 128/322, 323, 329 R, 334 R, 346, 399

[56] References Cited

U.S. PATENT DOCUMENTS

| | | | |
|---|---|---|---|
| 2,384,697 | 9/1945 | Riccardi | 128/346 |
| 3,492,994 | 2/1970 | Field | 128/346 |
| 3,503,396 | 3/1970 | Pierie et al. | 128/346 |
| 3,503,397 | 3/1970 | Fogarty et al. | 128/346 |
| 3,503,398 | 3/1970 | Fogarty et al. | 128/346 |
| 3,716,056 | 2/1973 | Brodsky et al. | 128/305 |
| 4,164,225 | 8/1979 | Johnson et al. | 128/334 R |
| 4,200,088 | 4/1980 | Denniston, Jr. | 128/303 R |
| 4,213,460 | 7/1980 | Weiner | 128/399 |

Primary Examiner—John J. Wilson
Attorney, Agent, or Firm—Townsend and Townsend

[57] ABSTRACT

An instrument comprised of a pair of relatively shiftable clamp members mounted on the outer ends of a pair of pivotally interconnected arms defining a forceps. The clamp members, when contiguous to each other, define a tubular space for receiving a portion of the scrotum containing the vas deferens, whereby the vas deferens is captured in the space and held by the clamp members when the clamp members are in their closed positions. One of the clamp members has a needle-receiving passage therethrough which intersects the central axis of the tubular passage so that, when a hypodermic needle is inserted in the passage, it can penetrate the scrotum and enter the vas deferens so that a sclerosing fluid carried by the needle can be injected into the vas deferens to block the flow of sperm therethrough. A second embodiment of the instrument includes a pair of needle-receiving passages on opposite sides of the central part of the passage which receives the scrotum and vas deferens.

10 Claims, 6 Drawing Figures

INSTRUMENT FOR USE IN OBSTRUCTING THE VAS DEFERENS

BACKGROUND OF THE INVENTION

1. Field of the Invention

This invention relates to improvements in surgical techniques involving the human anatomy and, more particulary, to an improved instrument for performing a vasectomy.

2. Description of the Prior Art

It is a normal surgical procedure performing a vasectomy to sever the vas deferens located in the scrotum. This surgical procedure generally requires a local anesthetic and incapacitates the patient for at least several hours until the effects of the anesthesia have worn off. Moreover, such a surgical technique requires one or more incisions which require a healing period and cause discomfort to the patient during the healing period. Because of these various drawbacks relating to conventional techniques for performing vasectomies, a need has arisen for an improved method and device for performing a vasectomy so that the vasectomy can be effected in a relatively short time with substantially no discomfort to the patient and without incapacitating the patient.

Prior patents relating to various instruments containing clamps and the like for surgical operations include the following U.S. patents:

| | |
|---|---|
| 2,384,697 | 3,503,298 |
| 3,378,010 | 3,716,056 |
| 3,492,994 | 4,200,088 |
| 3,503,396 | 4,213,460 |
| 3,503,397 | |

SUMMARY OF THE INVENTION

The present invention satisfies the aforesaid need by providing an improved instrument and method for performing a vasectomy wherein the instrument comprises a pair of relatively shiftable clamping members movable into and out of clamping positions contiguous to each other. The clamping members are on the outer ends of a forceps so that the instrument can be manually manipulated. When the clamp members are in their clamping positions, they define a tubular passage which receives the part of the scrotum containing the vas deferens so that the vas deferens is captured in the space and releasably held by the clamp members themselves.

One of the clamp members has a needle-receiving passage therethrough which is aligned with and intersects at least a portion of the central axis of the tubular space. Thus, when a needle is inserted into the passage as the clamp members retain the vas deferens in the tubular passage, the needle will pass into the scrotum, and into the vas deferens. When this occurs, the needle can be used to inject a sclerosing fluid into the vas deferens to block the flow of sperm through it. Then the needle is retracted and the vasectomy is complete.

As an alternate embodiment, the instrument can have a pair of needle-receiving passages. Such a modified instrument will be suitable for use when the anatomy of the patient requires some intricate manipulation or positioning of the instrument to accommodate different anatomical patterns in the patient himself.

The primary object of the present invention is to provide an instrument and method of performing a vasectomy wherein the portion of the scrotum containing the vas deferens is clamped in a confined space, following which a hypodermic needle containing a sclerosing fluid is guided through a passage and into the vas deferens and caused to inject the sclerosing fluid into the vas deferens itself, whereby the sclerosing fluid will block the flow of sperm through the vas deferens to thereby avoid the need to sever the vas deferens as has been done in the past to effect a vasectomy.

Other objects of this invention will become apparent as the following specification progresses, reference being had to the accompanying drawings for an illustration of the invention.

IN THE DRAWINGS

DETAILED DESCRIPTION OF THE PRESENT INVENTION

Figure 1:
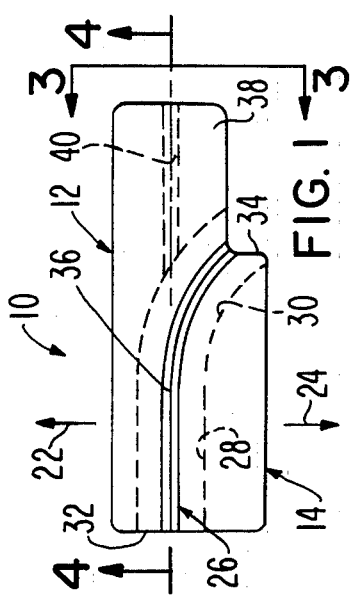
FIG. 1 is a top plan view of the instrument of the present invention.

A first embodiment of the instrument of the present invention as broadly denoted by the numeral 10 and includes a pair of relatively shiftable clamp members 12 and 14 which are secured to the outer ends of a pair of relatively shiftable arms 16 and 18, the arms defining a forceps which is manually held at its outer end to permit pivoting of the arms in a scissors like fashion to move the clamp members toward and away from each other. Arms 16 and 18 are pivotally coupled by a pin 20 (FIG. 2), and, when the clamp members 12 and 14 move away from each other, they move in the direction of arrows 22 and 24, respectively, (FIGS. 1 and 3).

Figure 3:
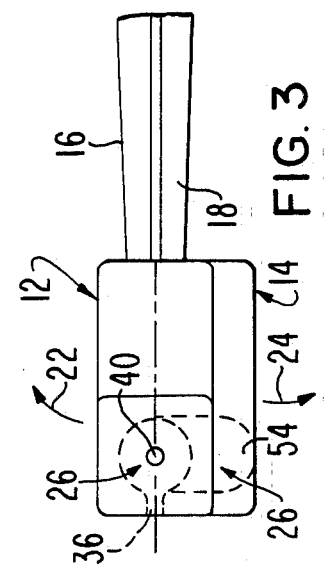
FIG. 3 is an end elevational view of the instrument of FIGS. 1 and 2, looking into the direction of line 3—3 of FIG. 1.
Figure 2:
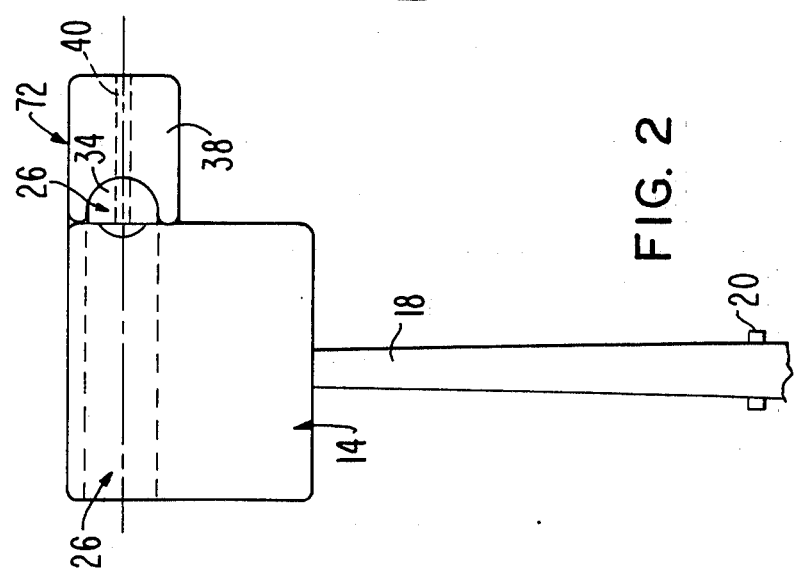
FIG. 2 is a side elevational view of the instrument, portions being broken away to simplify the drawings.
Figure 4:
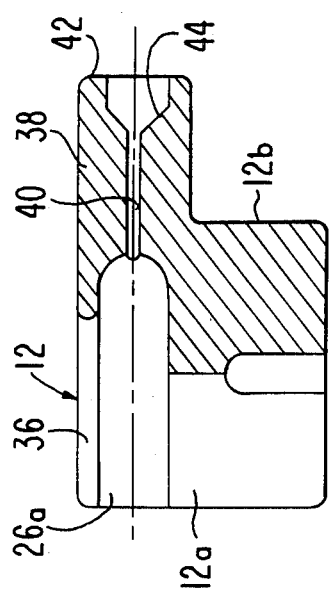
FIG. 4 is a cross sectional view taken along line 4—4 of FIG. 1.

Members 12 and 14, when they are in their closed or clamping positions, as shown in FIGS. 1-3, define an elongated tubular space 26 which has a relatively straight segment 28 and a curved segment 30 (FIG. 1). The space 26 is preferably circular in cross section. The space is open at its ends, one opening being denoted by the numeral 32 and the other opening being denoted by the numeral 34. Space 26 is adapted to receive a portion of the scrotum, especially the part which contains the vas deferens through which the sperm travels. The scrotum portion to be held by instrument 10 is placed between clamp members 12 and 14 when the same are separated from each other. Upon closing of the clamp members, the scrotum portion and the vas deferens are captured in space 26 with the vas deferens generally centrally located along the axial length of the space. The clamp members have reduced portions near one face of instrument 10 for defining a relief slot 36 through which the remainder of the scrotum can extend when only a portion of the scrotum is captured in space 26. FIG. 4 shows the hollowed-out part in a side face 12a of clamp member 12, this hollowed part being denoted by the numeral 26a and defining one half of the space 26 when the clamp members are closed as shown in FIGS. 1 and 3.

Clamp member 12 has a lateral projection 38 which extends from the main body portion 12b thereof. Extension 38 has a needle-receiving passage 40 therethrough, the ends of the passage 40 being open. The outer end of face 42 of extension 38 has a countersunk hole 44 to assist in guiding a hypodermic needle into passage 40. The inner end of passage 40 is open to space portion 26a so that a needle can be inserted into passage 26 when clamp members 12 and 14 are in their closed positions as shown in FIG. 1. Passage 40 has a longitudinal axis which is coincident with or at least intersects the central axis of space 26. This feature assures that the hypodermic needle will first enter the scrotum in space 26 and then enter the vas deferens when the needle is urged into and through passage 40. Thus, a sclerosing fluid carried by the hypodermic needle can be injected into the vas deferens for blocking the flow of sperm therethrough.

In use, clamp members 12 and 14 are opened or separated from each other by manipulation of the forceps. The clamp members are then moved into proximity to the scrotum portion containing the vas deferens, then the clamp members are closed on the scrotum portion such that the vas deferens extends substantially within and along the central axis of space 26. Since passage 40 is coincident with or intersects a segment of the central axis of space 26 as shown in FIG. 3, it will direct a needle into the vas deferens.

The needle is inserted into the passage 40, through the scrotum and into the vas deferens. Manipulation of the needle will then cause the sclerosing fluid carried by the needle to be injected into the vas deferens. Then the needle is retracted and clamping members 12 and 14 are separated from each other to release the scrotum portion initially captured in space 26.

Figure 5:
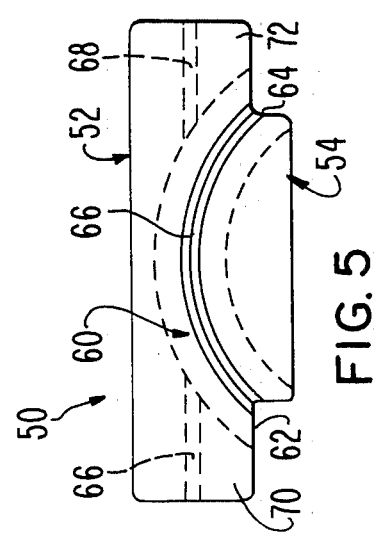
FIG. 5 is a view similar to FIG. 1 but showing a modification of the instrument.
Figure 6:
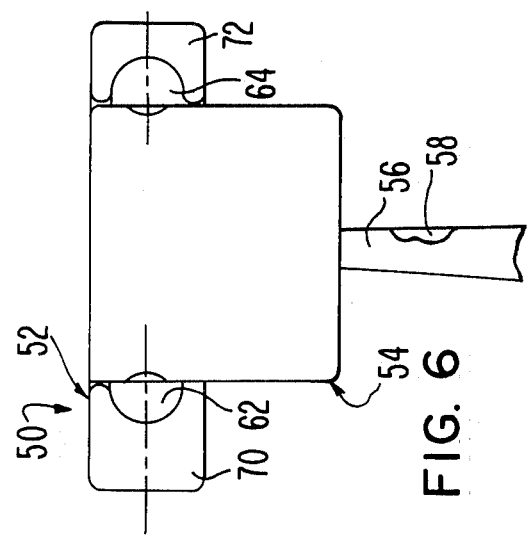
FIG. 6 is a view similar to FIG. 2 but showing the modified instrument of FIG. 5.

A modified embodiment of the present invention is shown in FIGS. 5 and 6 and is denoted by the numeral 50. Instrument 50 includes a pair of clamping members 52 and 54 secured to a pair of arms 56 and 58 (FIG. 6), the arms defining a forceps in the same manner as arms 16 and 18 of instrument 10.

Clamp members 52 and 54, when they are closed as shown in FIG. 5, define a curved, tubular space 60 having open ends 62 and 64 and a skin relief slot 66. Instrument 50 differs from instrument 10 in that instrument 50 has a pair of needle-receiving passages 66 and 68; whereas, instrument 10 only has a single needle-receiving passage 40. Passages 66 and 68 are formed in lateral extensions 70 and 72, respectively, on clamp member 52. The pair of passages 66 and 68 are provided for the convenience of the user as well as the need to be able to orient the instrument to render it suitable for the particular anatomy of a patient. Instrument 50 is used in substantially the same manner as instrument 10 so that the description above with respect to the use of instrument 10 applies equally well to that of instrument 50.

The embodiments of the instrument of the present invention are formed from a suitable metallic material which can easily be autoclaved and can be used without special skills. The instrument could also possibly be manufactured using cast or injected plastic so as to be disposable after a single use. The instrument of the present invention allows a vasectomy to be performed in a minimum of time and with a minimum of discomfort to the patient.

I claim:

1. An instrument for use in performing a vasectomy comprising:
   a pair of clamp members; and
   means coupled to the clamp members for moving the same into and out of positions adjacent to each other, said clamp members having means defining an elongated space when the clamp members are in said positions, said space having a shape adapted to receive and to confine an elongated portion of the scrotum containing the vas deferens, one of the clamp members having means for guiding a hypodermic needle into and longitudinally of the space and into the scrotum portion and the vas deferens when the scrotum portion is in the space.

2. An instrument as set forth in claim 1, wherein said means for moving said clamp members includes a forceps.

3. An instrument as set forth in claim 1, wherein said clamp members define a skin relief slot communicating with said space when the clamp members are in said positions.

4. An instrument for use in performing a vasectomy comprising:
   a pair of clamp members; and
   means coupled to the clamp members for moving the same into and out of positions adjacent to each other, said clamp members defining a space when the clamp members are in said positions, said space adapted to receive and to confine a portion of the scrotum containing the vas deferens, one of the clamp members having a lateral extension providing a needle-receiving passage extending therethrough for guiding a hypodermic needle into the space and into the scrotum portion and the vas deferens when the scrotum portion is in the space.

5. An instrument as set forth in claim 4, wherein the space is generally circular in cross section, the longitudinal axis of the passage being in intersecting relationship to a portion of the central axis of the space.

6. An instrument for use in performing a vasectomy comprising:
   a pair of clamp members; and
   means coupled to the clamp members for moving the same into and out of positions adjacent to each other, said clamp members defining a space when the clamp members are in said positions, said space having a rectilinear segment and a curved segment and adapted to receive and to confine a portion of the scrotum containing the vas deferens, one of the clamp members having an extension provided with a needle-receiving passage therethrough, said passage having an axis generally coincident with the central axis of said rectangular segment of the space for guiding a hypodermic needle into the space and into the scrotum portion and the vas deferens when the scrotum portion is in the space.

7. An instrument for use in performing a vasectomy comprising:
   a pair of clamp members; and
   means coupled to the clamp members for moving the same into and out of positions adjacent to each other, said clamp members defining a space when the clamp members are in said positions, said space having a pair of opposed open ends, the space being curved between said ends and adapted to receive and to confine a portion of the scrotum containing the vas deferens, there being a pair of lateral extensions on opposed sides of one of the clamp members, each extension having a needle-receiving passage communicating with said space for guiding a hypodermic needle into the space and into the scrotum portion and the vas deferens when the scrotum portion is in the space.

8. An instrument as set forth in claim 7 wherein said passages have a common axis.

9. A method of performing a vasectomy comprising:
confining a portion of the scrotum containing the vas deferens in a space;

guiding a hypodermic needle into the vas deferens when said scrotum portion is confined in said space; and injecting a sclerosing fluid into the vas deferens after the needle has been guided into the vas deferens.

10. A method as set forth in claim 7, wherein said confining step includes clamping the scrotum portion against movement relative to a predetermined reference.

* * * * *